(12) United States Patent
Feierabend et al.

(10) Patent No.: US 6,838,006 B2
(45) Date of Patent: Jan. 4, 2005

(54) OIL FIELD SEPARATION FACILITY CONTROL SYSTEM UTILIZING TOTAL ORGANIC CARBON ANALYZER

(75) Inventors: Jerry Glynn Feierabend, Katy, TX (US); David J. Blumer, Bartlesville, OK (US); Thomas Austin, Eagle River, AK (US); Sung-I Johnson, Houston, TX (US); Richard D. Sloan, Soldotna, AK (US); Bradley A. Neugebauer, Anchorage, AK (US); Randall Lee Heald, Bartlesville, OK (US); Mark F. Jerling, Waukesha, WI (US); Peter M. Bradshaw, Anchorage, AK (US)

(73) Assignee: ConocoPhillips Company, Houston, TX (US)

( * ) Notice: Subject to any disclaimer, the term of this patent is extended or adjusted under 35 U.S.C. 154(b) by 2 days.

(21) Appl. No.: 10/426,604

(22) Filed: Apr. 30, 2003

(65) Prior Publication Data
US 2004/0217065 A1 Nov. 4, 2004

(51) Int. Cl.⁷ .................................................. C02F 1/40
(52) U.S. Cl. ........................ 210/739; 210/747; 210/96.1
(58) Field of Search ................................ 210/739, 747, 210/800, 96.1, 143, 170, 513; 73/61.43, 61.44; 166/264

(56) References Cited

U.S. PATENT DOCUMENTS

| | | | |
|---|---|---|---|
| 4,619,771 A | | 10/1986 | Stall et al. |
| 4,637,464 A | * | 1/1987 | Forgac et al. ............... 106/261 |
| 4,983,287 A | | 1/1991 | Arnold |
| 5,104,545 A | | 4/1992 | Means et al. |
| 5,106,754 A | * | 4/1992 | Steele et al. ................ 436/146 |
| 5,518,608 A | * | 5/1996 | Chubachi ................... 210/96.1 |
| 5,868,945 A | | 2/1999 | Morrow et al. |
| 5,873,997 A | * | 2/1999 | Kaplan ....................... 210/150 |
| 6,398,966 B1 | | 6/2002 | Smith et al. |
| 6,491,824 B1 | * | 12/2002 | Lin et al. .................... 210/666 |
| 6,620,329 B2 | * | 9/2003 | Rosen et al. ................ 210/739 |
| 2004/0079706 A1 | * | 4/2004 | Mairal et al. ............... 210/651 |

FOREIGN PATENT DOCUMENTS

JP 2002-282852 A * 10/2002

* cited by examiner

Primary Examiner—Frank M. Lawrence
(74) Attorney, Agent, or Firm—Kameron D. Kelly; Ryan N. Cross

(57) ABSTRACT

An oil field separation facility utilizing a total organic carbon analyzer to help maintain consistently acceptable levels of oil and water separation. The facility separates a produced oil and water mixture into an oil-rich stream and a water-rich stream. The total organic carbon analyzer measures the total organic carbon content of the water-rich stream. The measured total organic carbon content of the water-rich stream can then be used to adjust an operating parameter of the separation facility.

36 Claims, 3 Drawing Sheets

BY-PASS MODE

SAMPLING MODE

OIL FIELD SEPARATION FACILITY CONTROL SYSTEM UTILIZING TOTAL ORGANIC CARBON ANALYZER

BACKGROUND OF THE INVENTION

1. Field of the Invention

The present invention relates generally to facilities for separating oil and water present in a fluid mixture produced from a subterranean well. In another aspect, the invention concerns a system for controlling an oil field separation facility by measuring the amount of oil present in the separated water stream.

2. Description of the Prior Art

Oil wells frequently produce water along with oil. In many instances the commonly produced oil and water phases are separated in the field prior to transporting the oil to a major pipeline or refinery facility. Each in-the-field oil separation facility may service a number of individual wells. Thus, large volumes of oil and water may be passed through the separation facility every day. If the separation facility does not properly separate the oil and water, either the oil stream exiting the facility will contain too much water or the water stream exiting the facility will contain too much oil. If too much water is contained in the separated oil stream exiting the facility, the oil stream may be rejected by the operator of the pipeline and/or the refinery. If too much oil is contained in the separated water stream exiting the facility, the value of the oil present in the water stream is lost because typically the separated water stream is simply discharged or reinjected into the subterranean formation for water flooding. For large separation facilities, an oil content of just 5,000 ppmw in the separated water stream can result in a yearly oil loss valued at several million dollars.

In the past, the oil content of the separated water stream from oil field separation facilities has been measured on a relatively infrequent (typically daily) basis. However, it has recently been discovered that the amount of oil in the separated water stream can vary greatly by the hour or minute. Thus, measuring the oil content of the separated water stream on an infrequent basis may not provide a reliable indication of oil content because limited duration spikes in the oil content may not be accounted for. Also, infrequent measurement of the oil content does not allow the separation facility to be controlled in a dynamic manner which can reduce or eliminate spikes in the oil concentration. An additional drawback of many conventional methods for measuring the oil content of a separate water stream is that past methods of sampling the separated water stream are somewhat suspect because they did not account for the tendency of the oil and water phases to separate from one another. Thus, conventional sampling methods drawing from a certain location in the separated water conduit may provide a poor representation of the actual content of oil in the separated water stream.

In the past, ultraviolet or visible fluorescence analyzers have been used to measure the oil content of diluted water discharged from separation facilities. These conventional analyzers are designed to measure much lower concentrations of oil (e.g., 10–50 ppmw) than are present in the undiluted separated water stream from the separation facility. Thus, because these conventional analyzers are not designed for the application proposed herein, they present a number of drawbacks. For example, these conventional analyzers are extremely sensitive to the amount of oil in the separated water stream and, therefore, would require high amounts of dilution (e.g., 100–10,000×) of the separated water sample in order to reduce the oil content of the analyzed sample down to a measurable level. Such high dilution rates result in a less accurate measurement due in part to trace amounts of organic contaminants present in the diluent. In addition, these conventional analyzers are designed for single phase fluids, rather than the 2-phase oil-in-water dispersions that are typical in the separated water stream. It is even more difficult for these conventional analyzers to provide an accurate measurement from a highly diluted sample because of the difficulty involved in providing uniform dispersions of oil in highly diluted water samples. Further, conventional analyzers must be recalibrated every time the composition of the oil in the separated water stream changes because conventional analyzers only measure a certain narrow range of oil compositions.

OBJECTS AND SUMMARY OF THE INVENTION

It is, therefore, an object of the present invention to provide an oil field separation facility control system that frequently measures the oil content in the separated water stream and adjusts operating parameters of the separation facility in real time based on the measured oil content of the separated water stream.

Another object of the present invention is to provide a system for more accurately sampling the separated water stream produced from an oil field separation facility.

Still another object of the present invention is to provide a system for analyzing the amount of oil in a water stream that does not require high rates of dilution of the separated water sample.

Yet another object of the present invention is to provide a system for analyzing the amount of oil in a water stream that can accurately analyze a 2-phase oil-in-water dispersion.

A further object of the present invention is to provide a system for analyzing the amount of oil in a water stream that does not require recalibration of the analyzer when the composition of the oil is varied.

It should be understood that the above-listed objects are only exemplary, and not all the objects listed above need be accomplished by the invention described and claimed herein.

Accordingly, in one embodiment of the present invention, there is provided a method comprising the steps of: (a) separating a mixture of oil and water into an oil-rich stream and a water-rich stream, the water-rich stream containing organic compounds; (b) measuring the total organic carbon content of the water-rich stream; and (c) adjusting the manner in which step (a) is performed based on the total organic carbon content measured in step (b).

In accordance with another embodiment of the present invention, there is provided a method of controlling an oil field separation facility that is operable to separate a produced oil and water mixture into a predominately oil stream and a predominately water stream. The method comprises the steps of: (a) agitating the predominately water stream to thereby increase the turbulence of the predominately water stream; (b) continuously conducting a sample portion of the agitated predominately water stream to an analyzer system comprising a total organic carbon analyzer; (c) periodically measuring the total organic carbon content of the sample portion using the total organic carbon analyzer; and (d) adjusting at least one operating parameter of the separation facility based on the measured total organic carbon content of the sample portion.

In accordance with yet another embodiment of the present invention, there is provided a method comprising the steps of: (a) conducting a predominately water stream through a conduit, the predominately water stream comprising organic compounds; (b) continuously withdrawing a sample portion of the predominately water stream from the conduit; (c) continuously conducting the sample portion to an analyzer system comprising a defined sample volume, a defined diluent volume, and a total organic carbon analyzer; (d) periodically operating the analyzer system in a by-pass mode wherein the defined sample volume, the defined diluent volume, and the total organic carbon analyzer are fluidly isolated from one another; and (e) periodically operating the analyzer system in a sampling mode wherein the defined sample volume, the defined diluent volume, and the total organic carbon analyzer are in fluid flow communication with one another, the defined sample volume being fluidly disposed between the defined diluent volume and the total organic carbon analyzer.

In accordance with a still further embodiment of the present invention, there is provided an apparatus comprising separation equipment operable to separate a mixture of oil and water into an oil-rich stream and a water-rich stream, a water conduit for carrying the water-rich stream away from the separation equipment, and an analyzer system fluidly coupled to the water conduit and operable to measure the total organic carbon content of the water-rich stream.

BRIEF DESCRIPTION OF THE DRAWING FIGURES

A preferred embodiment of the present invention is described in detail below with reference to the attached drawing figures, wherein.

Figure 3:
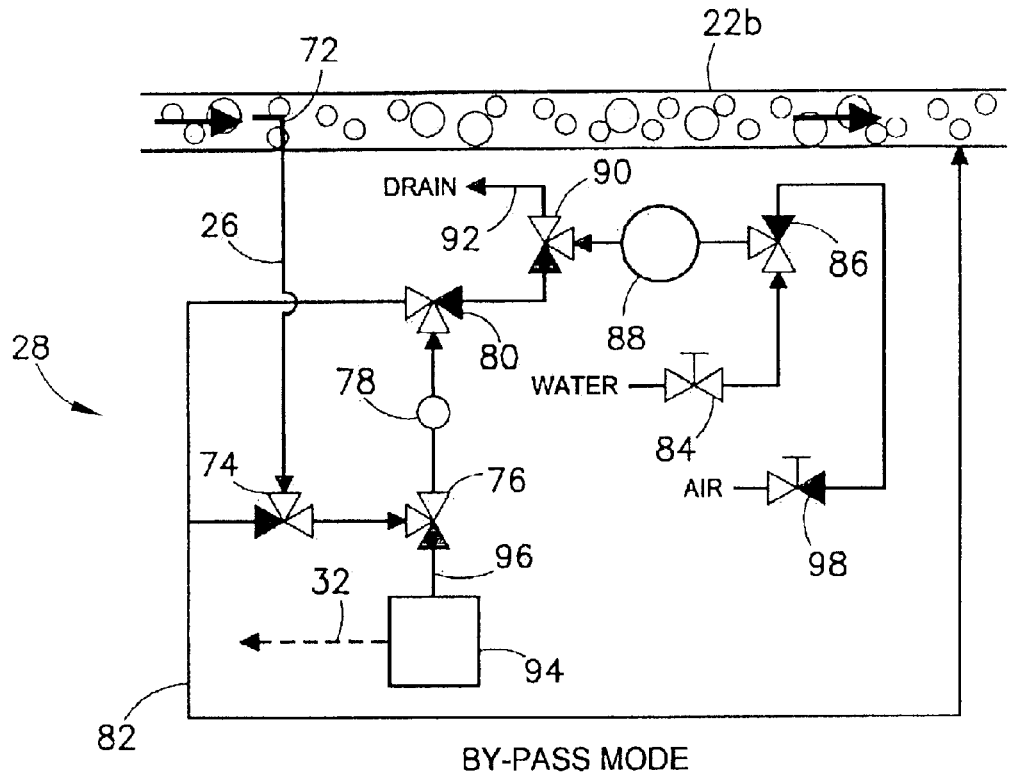
Figure 4:
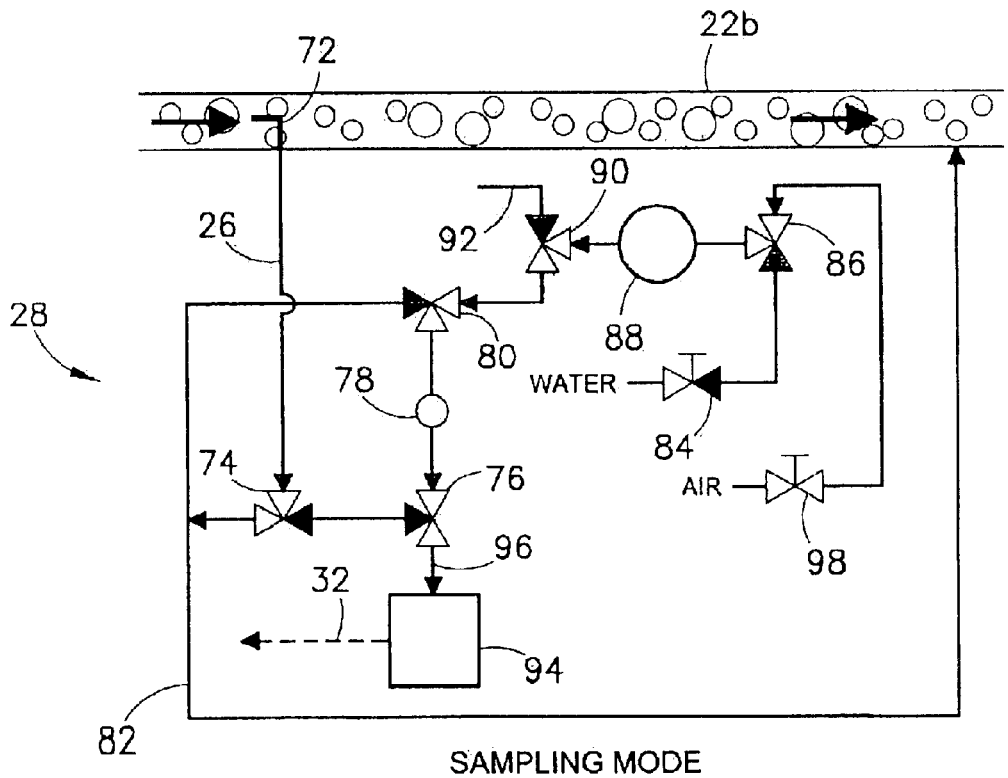

FIG. 3 is a schematic flow diagram of the analyzer system used to sample the separated water stream and determine the amount of oil in the separated water stream sample, particularly illustrating the analyzer system in a by-pass mode where a sample of the separated water stream is not being charged to the total organic carbon analyzer; and FIG. 4 is a schematic flow diagram of the analyzer system of FIG. 3, particularly illustrating the analyzer system in a sampling mode where a sample of the separated water stream is being charged to the total organic carbon analyzer.

DETAILED DESCRIPTION OF THE PREFERRED EMBODIMENT

Figure 1:
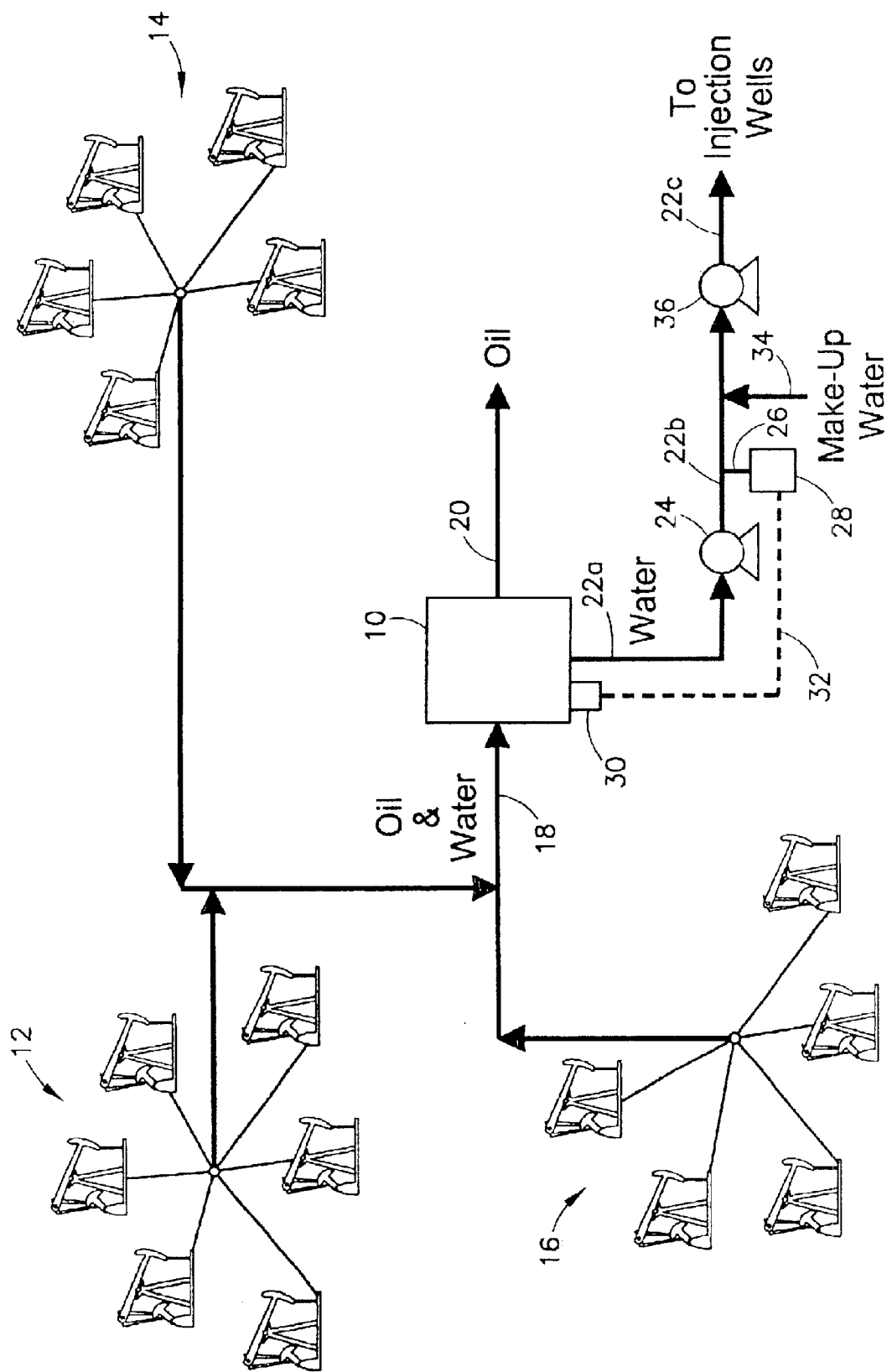
FIG. 1 is a schematic representation of an oil field separation facility servicing several different oil fields that each contain a number of individual oil wells.

Referring initially to FIG. 1, an oil field separation facility 10 is illustrated as servicing several different oil fields, each including a number of individual wells. Produced oil and water from a first oil field 12, a second oil field 14, and a third oil field 16 are combined in a main conduit 18 and carried to separation facility 10. Although FIG. 1 shows separation facility 10 servicing only 16 individual wells, it is more typical for oil field separation facility 10 to service a greater number of individual wells (e.g., 50–500 wells). In separation facility 10, the produced oil and water mixture is separated into an oil-rich stream exiting separation facility 10 via an oil conduit 20 and a water-rich stream exiting separation facility 10 via a water conduit 22a.

Water conduit 22a carries the water-rich stream to an agitating means 24 which is operable to increase the turbulence of the water-rich stream. Agitating means 24 can be any apparatus for enhancing the physical mixing of the oil present in the water-rich stream to thereby provide a more even dispersion of oil droplets in the water-rich stream. In a preferred embodiment of the present invention, agitating means 24 is a booster pump; however, agitating means 24 could also be a conventional static mixer. After being agitated in agitation means 24, the water-rich stream is conducted through water conduit 22b. A sample line 26 is fluidly coupled to water conduit 22b and is operable to withdraw a small portion of the water-rich stream from water conduit 22b. Sample line 26 carries the sampled portion of the water-rich stream to an analyzer system 28. Analyzer system 28, described in detail below with respect to FIGS. 3 and 4, includes a total organic carbon analyzer that measures the total organic carbon content of the sampled portion of the water-rich stream. The total organic carbon content measured in analyzer system 28 provides a reliable and accurate indication of the amount of oil present in the water-rich stream, regardless of the composition of the oil in the water-rich stream. The total organic carbon content value measured in analyzer system 28 can be communicated to a controller 30 via a communication means 32. Controller 30 is operably coupled to separation facility 10 and functions to control at least one operating parameter of separation facility 10. Preferably, the operating parameter or parameters of separation facility 10 that is/are controlled by controller 30 can be adjusted to vary the amount of oil present in the water-rich stream exiting separation facility 10 via water conduit 22a. Communication means 32 can be any system for communicating information between two locations. For example, communication means 32 could be electrically conductive wires, fiber optic lines, or a wireless transmission system.

In a preferred embodiment of the present invention, a sample of the water-rich stream is continuously withdrawn from water conduit 22b via sample line 26. As used herein, the term "continuous" shall denote an operation that is continually performed for uninterrupted periods of at least 12 hours. The total organic carbon content of the continuously withdrawn water-rich sample can then be either continuously or periodically measured in analyzer system 28. As used herein, the term "periodically" shall denote an operation that is performed at intervals of less than 12 hours. Preferably, analyzer system 28 periodically measures the total organic carbon content of the sampled water-rich stream at intervals of less than about 6 hours, more preferably less than about 1 hour, still more preferably less than about 0.25 hours, and most preferably less than 0.1 hours. Thus, a signal indicating the current oil content in the water-rich stream can continually, or at least frequently, be provided to controller 30, which can then vary the manner in which separation facility 10 operates to thereby optimize the separation process.

Typically, the total organic carbon content measured by analyzer system 28 will be compared to a predetermined maximum total organic carbon content value in order to determine whether or not an operating parameter of separation facility 10 needs to be adjusted. If the total organic carbon content measured by analyzer system 28 exceeds the predetermined maximum total organic content value, controller 30 will adjust separation facility 10 so that less oil is present in the water-rich stream exiting separation facility 10 via water conduit 22a. Preferably, the predetermined maximum total organic content value is equivalent to an oil content in the water-rich stream in the range of from about 100 to about 10,000 ppmw (parts per million by weight), most preferably 1,000 to 5,000 ppmw.

After a portion of the water-rich stream in water conduit 22b is withdrawn via sample line 26, make-up water from conduit 34 can be added to the water-rich stream in water conduit 22b. The combined make-up water and water-rich stream can then be carried to an injection pump 36 which increases the pressure of the stream to a level sufficient for injection into injection wells via water conduit 22c. The water stream conducted to the injection wells is typically used for water flood operations in oil fields 12, 14, and 16, or other oil fields.

Figure 2:
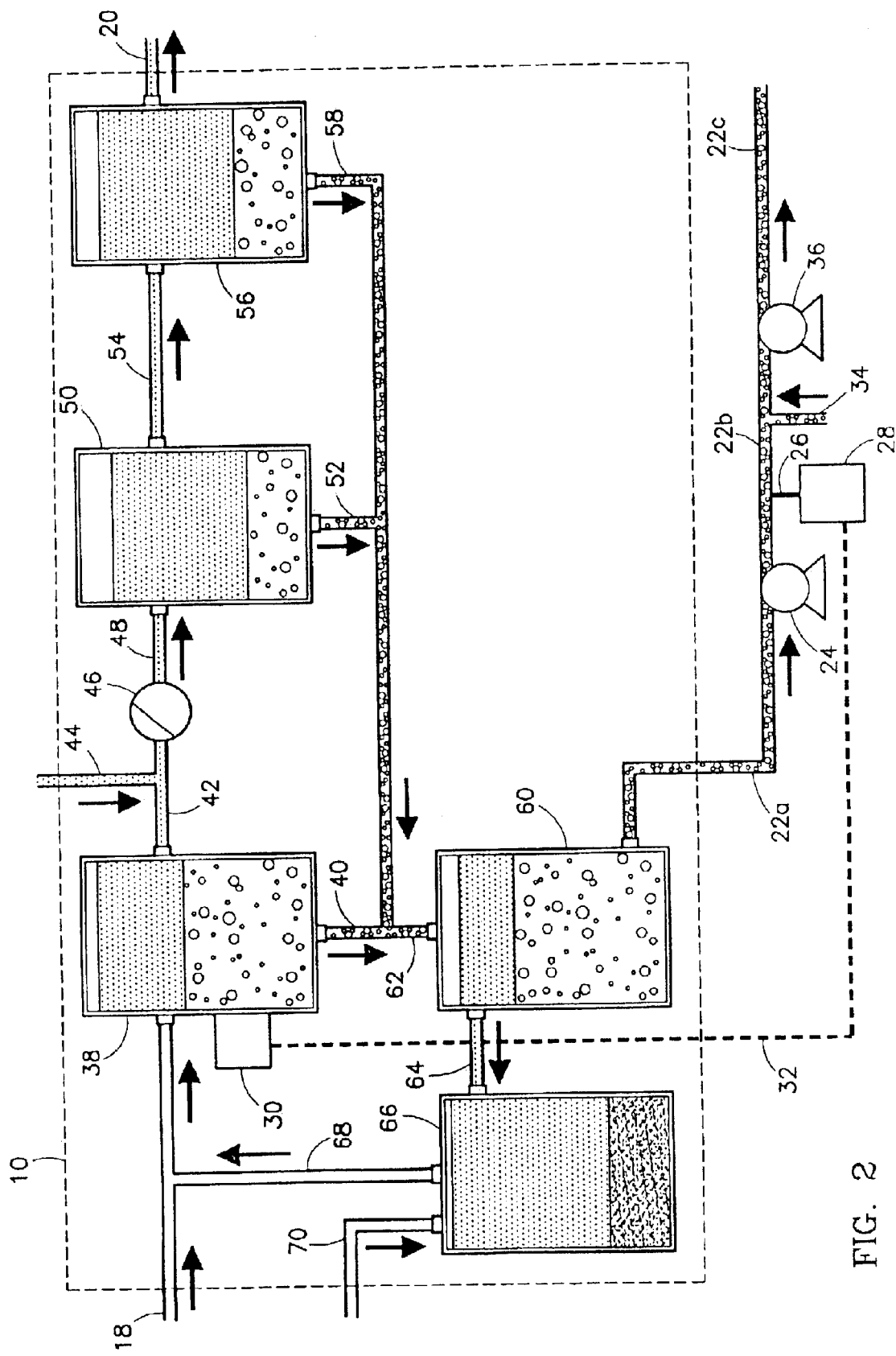
FIG. 2 is a more detailed representation of the oil field separation facility of FIG. 1, particularly illustrating the configuration of the separation equipment as well as a system for measuring the oil content of the separated water stream.

Referring to FIG. 2, a preferred configuration of separation equipment in separation facility 10 is illustrated in greater detail. It should be understood that FIG. 2 illustrates just one of many configurations of the separation equipment that can be employed in separation facility 10. The embodiment illustrated in FIG. 2 shows the produced oil and water mixture entering separation facility 10 via main conduit 18. The produced oil and water mixture is first carried to a primary separator 38 where the oil and water are separated, with the water portion exiting primary separator 38 via conduit 40 and the oil portion exiting primary separator 38 via conduit 42. Optionally, a wet oil stream in conduit 44 can be combined with the separated oil-rich stream in conduit 42 and then sent to a crude heater 46. From crude heater 46, the heated oil-rich stream can then be conducted via conduit 48 to a secondary separator 50. The separated water exits secondary separator 50 via conduit 52, while the separated oil exits secondary separator 50 via conduit 54. The oil-rich stream in conduit 54 is then introduced into an electrostatic coalescer 56 wherein a remaining portion of water is separated from the oil. The separated water exits electrostatic coalescer 56 via conduit 58, while the separated oil-rich stream exits electrostatic coalescer 56 and separation facility 10 via oil conduit 20. Preferably, the separated oil-rich stream in oil conduit 20 contains less than about 5 volume percent water, more preferably less than about 2 volume percent water, still more preferably less than 1 percent water, and most preferably less than 0.5 volume percent water.

The separated water-rich streams in conduits 40, 52, and 58 are combined and carried to a produced water tank 60 via conduit 62. In produced water tank 60, oil and water phases are separated, with the skimmed oil exiting produced water tank 60 via conduit 64 and the water-rich stream exiting produced water tank 60 and separation facility 10 via water conduit 22a. The skimmed oil in conduit 64 is carried to a slop oil tank 66 where the oil is separated from sand present therein. The separated oil from slop oil tank 66 can be conducted to main conduit 18 via conduit 68, where it is combined with the produced oil and water mixture entering primary separator 38. Slop oil tank 66 can also receive trucked-in recycle hydrocarbon fluids via conduit 70.

As described above with reference to FIG. 1, the water-rich stream in water conduit 22a is first agitated in agitating means 24, then sampled via sample line 26, then combined with make-up water from make-up water conduit 34, and finally pumped from injection pump 36 to injection wells via water conduit 22c. FIG. 2 shows that the total organic carbon analyzer system 28 can communicate with controller 30 via communication means 32. In the embodiment illustrated in FIG. 2, controller 30 is operable to vary the manner in which primary separator 38 functions, to thereby adjust the amount of oil in the water-rich stream exiting separation facility 10 via water conduit 22a. Although controller 30 is illustrated in FIG. 2 as varying an operating parameter of primary separator 38, it should be understood that controller 30, or a number of different controllers, can be used at a number of different locations in separation facility 10 to control the amount of oil present in the water-rich stream which ultimately exits separator facility 10 via water conduit 22a.

Referring now to FIGS. 3 and 4, the components that make up analyzer system 28 are illustrated in greater detail. FIG. 3 shows analyzer system in a by-pass mode, while FIG. 4 shows analyzer system 28 in a sampling mode. In both modes, a quill 72 is disposed in water conduit 22b and continuously samples a portion of the water-rich stream. Preferably, quill 72 extends into water conduit 22b to thereby withdraw the sample of the water-rich stream from about the middle of water conduit 22b. The sampled portion of the water-rich stream is then carried to analyzer system 28 via sample line 26.

Referring to FIG. 3, when analyzer system 28 is operated in the by-pass mode, the sampled portion of the water-rich stream in sample line 26 is continuously conducted through a first sample valve 74, a second sample valve 76, a defined sample volume 78, a third sample valve 80, and a by-pass conduit 82. By-pass conduit 82 can be routed back to water conduit 22b. Alternatively, by-pass conduit 82 can be routed to a drain. First, second, and third sample valves 74, 76, and 80 are preferably electronically controlled 3-way valves. Defined sample volume 78 can be any container or conduit that defines a specific volume through which the sampled portion of the water-rich stream can continuously pass during the by-pass mode. Referring to FIG. 3, when analyzer system 28 is operated in the by-pass mode, a diluent, such as water, is passed through a first diluent valve 84, a second diluent valve 86, a defined diluent volume 88, a third diluent valve 90, and a drain conduit 92. First diluent valve 84 is preferably an electronically controlled 2-way valve. Second and third diluent valves 86 and 90 are preferably electronically controlled 3-way valves. Defined diluent volume 88 can be any container or conduit that defines a specific volume through which the diluent (e.g., water) can be passed when analyzer system 28 is operated in the by-pass mode. It is preferred for the diluent to comprise substantially no organic compounds. It is further preferred for the volume of defined diluent volume 88 to be about 1 to about 100 times greater than the volume of defined sample volume 78, more preferably about 4 to about 25 times greater, and most preferably 6 to 12 times greater.

FIG. 3 depicts analyzer system 28 as including a total organic carbon analyzer 94 which is fluidly connected to second sample valve 76 via sample line 96. When analyzer system 28 is operated in the by-pass mode, second sample valve 76 prevents any of the sampled portion of the water-rich stream from entering total organic carbon analyzer 94. It can be seen from FIG. 3 that when analyzer system 28 is operated in the by-pass mode, defined diluent volume 88, defined sample volume 78, and total organic content analyzer 94 are fluidly isolated from one another. Total organic carbon analyzer 94 can be any conventional total organic carbon analyzer known in the art. Preferably, total organic carbon analyzer 94 is operable to receive a defined volume of a liquid sample, oxidize the organic components of the liquid sample, and measure the carbon dioxide formed via oxidization of the organic compounds in the liquid sample. The measured total organic carbon content of the liquid sample can then be communicated to a control device via communication means 32. Various total organic carbon analyzers are well known in the art. A particularly preferred total organic carbon analyzer is available from Star Instruments, Inc., League City, Tex. under the commercial designation of "Ultra Pure Pumpless Total Organic Carbon Analyzer Model 4000." As shown in FIG. 3, analyzer system 28 further includes a gas valve 98 which controls the flow of a gas, typically air, to second diluent valve 86. Gas valve 98 is preferably an electronically controlled 2-way valve. When analyzer system 28 is operated in the by-pass mode, gas valve 98 prevents the gas from flowing to second diluent valve 86.

FIG. 4 shows analyzer system 28 operating in the sampling mode. When analyzer system 28 is switched from the by-pass mode in FIG. 3 to the sampling mode in FIG. 4, each of valves 74, 76, 78, 80, 84, 86, 90, and 98 are adjusted. When analyzer system 28 operates in the sampling mode, the sampled portion of the water-rich stream from water conduit 22b is continuously carried through sample line 26, first sample valve 74, and by-pass line 82. The sampled portion in by-pass line 82 can then be routed back to conduit 22b for combining with the water-rich stream. Alternatively, the sampled portion in by-pass conduit 82 can be routed to a drain. It can be seen from FIG. 4 that when analyzer system 28 operates in the sampling mode, defined diluent volume 88, defined sample volume 78, and total organic content analyzer 94 are in fluid flow communication with one another, with defined sample volume 78 being fluidly disposed between defined diluent volume 88 and analyzer 94.

When analyzer system 28 is switched from the by-pass mode (FIG. 3) to the sampling mode (FIG. 4), a gas is conducted through gas valve 98, second diluent valve 86, defined diluent volume 88, third diluent valve 90, third sample valve 80, defined sample volume 78, second sample valve 76, and sample line 96. As such, the gas effectively pushes the diluent in defined diluent volume 88 and the water-rich sample in defined sample volume 78 into total organic carbon analyzer 94. The diluent from defined diluent volume 88 is used to flush the water-rich sample out of the defined sample volume 78. In total organic carbon analyzer 94, the diluent from defined diluent volume 88 and the water-rich sample from defined sample volume 78 are combined to produce a diluted sample. The volumetric ratio of defined sample volume 78 to defined diluent volume 88 can be determined by the amount of the diluent required to adequately flush the sample from defined sample volume 78, as well as the sensitivity of total organic content analyzer 94. It is preferred for the volume of defined diluent volume 88 to be 1 to 100 times greater than the volume of defined sample volume 78, more preferably 4 to 25 times greater, and most preferably 6 to 12 times greater. It is also preferred for analyzer system 28 to continuously switch back and forth between the by-pass mode and the sampling mode during normal operation. Preferably, analyzer switches between the by-pass and sampling modes at least every 12 hours, more preferably at least every 6 hours, still more preferably at least every 1 hour, yet still more preferably at least every 0.25 hour, and most preferably at least every 0.1 hour.

The preferred forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention.

The inventors hereby state their intent to rely on the doctrine of equivalents to determine and assess the reasonably fair scope of the present invention as it pertains to any apparatus not materially departing from but outside the literal scope of the invention as set forth in the following claims.

What is claimed is:

1. A method comprising:
    (a) separating a mixture of oil and water into an oil-rich stream and a water-rich stream, said water-rich stream containing organic compounds;
    (b) measuring the total organic carbon content of the water-rich stream; and
    (c) adjusting the manner in which step (a) is performed based on the total organic carbon content measured in step (b),
    step (b) including diluting a discrete volume of the water-rich stream with a diluent comprising substantially no organic compounds, thereby forming a diluted volume,
    step (b) including measuring the total organic carbon content of the diluted volume.

2. The method of claim 1,
    step (c) being operable to vary the amount of oil present in the water-rich stream.

3. The method of claim 1,
    step (b) being performed by a total organic carbon analyzer operable to oxidize the organic compounds present in the water-rich stream.

4. The method of claim 3,
    said total organic carbon analyzer being operable to measure the amount of carbon dioxide in the oxidized water-rich stream.

5. The method of claim 1,
    said diluted volume having a volumetric ratio of the water-rich stream to the diluent in the range of from about 1:1 to about 1:100.

6. The method of claim 1,
    said diluted volume having a volumetric ratio of the water-rich stream to the diluent in the range of from about 1:4 to about 1:25.

7. The method of claim 1,
    step (b) being performed at intervals of less than about 6 hours.

8. The method of claim 1,
    step (b) being performed at intervals of less than about 1 hour.

9. A method comprising:
    (a) separating a mixture of oil and water into an oil-rich stream and a water-rich stream, said water-rich stream containing organic compounds;
    (b) measuring the total organic carbon content of the water-rich stream;
    (c) adjusting the manner in which step (a) is performed based on the total organic carbon content measured in step (b); and
    (d) prior to step (b), physically agitating the water-rich stream to thereby increase the turbulence of the water-rich stream.

10. The method of claim 9, step (d) being performed by a pump.

11. The method of claim 9, and
    (e) prior to step (a), producing the mixture of oil and water from a subterranean formation.

12. The method of claim 11, and
    (f) subsequent to step (b), injecting the water-rich stream into the subterranean formation.

13. The method of claim 12, and
    (g) prior to step (f), adding make-up water to the water-rich stream.

14. A method of controlling an oil field separation facility, said separation facility being operable to separate a produced oil and water mixture into a predominately oil stream and a predominately water stream, said method comprising the steps of:
 (a) agitating the predominately water stream to thereby increase the turbulence of the predominately water stream;
 (b) continuously conducting a sample portion of the agitated predominately water stream to an analyzer system comprising a total organic carbon analyzer;
 (c) periodically measuring the total organic carbon content of the sample portion using the total organic carbon analyzer; and
 (d) adjusting at least one operating parameter of the separation facility based on the measured total organic carbon content of the sample portion.

15. The method of claim 14,
 step (d) being operable to vary the amount of oil present in the predominately water stream.

16. The method of claim 15, and
 (e) comparing the measured total organic carbon content of the predominately water stream with a predetermined maximum total organic carbon content value,
 step (d) including decreasing the amount of oil in the predominately water stream if the measured total organic carbon content of the predominately water stream exceeds the predetermined maximum total organic carbon content value.

17. The method of claim 16,
 said predetermined maximum total organic carbon content value representing an oil content in the predominately water stream of about 100 to about 10,000 ppmw.

18. A method comprising the steps of:
 (a) conducting a predominately water stream through a conduit, said predominately water stream comprising organic compounds;
 (b) continuously withdrawing a sample portion of the predominately water stream from the conduit;
 (c) continuously conducting the sample portion to an analyzer system comprising a defined sample volume, a defined diluent volume, and a total organic carbon analyzer;
 (d) periodically operating the analyzer system in a by-pass mode wherein the defined sample volume, the defined diluent volume, and the total organic carbon analyzer are fluidly isolated from one another; and
 (e) periodically operating the analyzer system in a sampling mode wherein the defined sample volume, the defined diluent volume, and the total organic carbon analyzer are in fluid flow communication with one another, said defined sample volume being fluidly disposed between the defined diluent volume and the total organic carbon analyzer.

19. The method of claim 18,
 step (d) including conducting the sample portion through the defined sample volume.

20. The method of claim 19,
 step (d) including conducting a diluent through the defined diluent volume,
 said diluent comprising substantially no organic compounds.

21. The method of claim 20,
 step (e) including conducting the sample portion in the defined sample volume and the diluent in the defined diluent volume to the total organic carbon analyzer,
 said sample portion from the defined sample volume and said diluent from the defined diluent volume being combined in the total organic carbon analyzer to thereby form a diluted sample.

22. The method of claim 21, and
 (f) measuring the total organic carbon content of the diluted sample in the total organic carbon analyzer.

23. The method of claim 21,
 step (e) including using the diluent in the defined diluent volume to force the sample portion in the defined sample volume out of the defined sample volume and into the total organic carbon analyzer.

24. The method of claim 21,
 step (e) including using a gas to force the diluent in the defined diluent volume and the sample portion in the defined sample volume into the total organic carbon analyzer.

25. The method of claim 21,
 said defined diluent volume being about 1 to about 100 times larger than the defined sample volume.

26. The method of claim 18,
 said analyzer system continuously alternating between the by-pass and sampling modes.

27. The method of claim 18,
 said analyzer system alternating between the by-pass and sampling modes at least every hour.

28. The method of claim 18, and
 (g) separating a mixture of oil and water into a predominately oil stream and the predominately water stream.

29. The method of claim 28, and
 (h) injecting the predominately water stream into a subterranean formation.

30. An apparatus comprising:
 separation equipment operable to separate a mixture of oil and water into an oil-rich stream and a water-rich stream;
 a water conduit for carrying the water-rich stream away from the separation equipment;
 an analyzer system fluidly coupled to the water conduit and operable to measure the total organic carbon content of the water-rich stream; and
 a fluid agitating means fluidly disposed in the water conduit between the separation equipment and the analyzer system and operable to increase the turbulence of the water-rich stream in the water conduit.

31. The apparatus of claim 30,
 said analyzer system including a quill at least partially disposed in the water conduit and operable to remove a sample portion of the water-rich stream from the water conduit.

32. The apparatus of claim 31,
 said analyzer system including a total organic carbon analyzer operable to measure the total organic carbon content of the sample portion by oxidizing the organic compounds in the sample portion and measuring the amount of carbon dioxide in the oxidized sample portion.

33. The apparatus of claim 32, and
 a controller operably coupled to the total organic carbon analyzer and the separation equipment, said controller being operable to adjust at least one operating parameter of the separation equipment based on the total organic carbon content measured by the total organic carbon analyzer.

34. The apparatus of claim 30, said fluid agitating means being a pump.

35. The apparatus of claim 30; and an injection pump fluidly disposed in the water conduit downstream of the analyzer system, said injection pump being operable to pump the water-rich stream into a subterranean formation.

36. The apparatus of claim 35, and a make-up water conduit fluidly coupled to the water conduit downstream of the analyzer system and upstream of the injection pump.

* * * * *